| United States Patent [19] | [11] 3,985,506 |
| --- | --- |
| Das | [45] Oct. 12, 1976 |

[54] REAGENT AND METHOD FOR DETERMINATION OF GLOBULIN

[75] Inventor: Manik L. Das, Crestwood, Mo.

[73] Assignee: Sigma Chemical Company, St. Louis, Mo.

[22] Filed: July 11, 1975

[21] Appl. No.: 595,239

[52] U.S. Cl. ............................... 23/230 B; 252/408
[51] Int. Cl.$^2$ .................. G01N 21/02; G01N 33/16
[58] Field of Search .................... 23/230 B; 252/408

[56] References Cited
UNITED STATES PATENTS

| 3,607,081 | 9/1971 | Goldenberg ........................ 23/230 B |
| 3,627,468 | 12/1971 | Goldenberg et al. ............... 23/230 B |

OTHER PUBLICATIONS

Dalby et al., *Anal. Biochem.*, v. 63, pp. 283–285 (1975).

*Primary Examiner*—Morris O. Wolk
*Assistant Examiner*—Timothy W. Hagan
*Attorney, Agent, or Firm*—Polster and Polster

[57] ABSTRACT

A stable reagent for use in a rapid and sensitive globulin estimation procedure consists of 60–70 volumes of glacial acetic acid, 1–20 volumes of monomethyl ether of ethylene glycol, 5–15 volumes of phosphoric acid, 5–15 volumes of sulfuric acid, 0.2–0.6 volumes of twenty percent glyoxylic acid in aqueous solution, and 0.4–1.2 volumes of ten pecent ferric chloride hexahydrate in aqueous solution. The reagent is far more stable, sensitive, and tolerant of water in the reaction mixture than previously known reagents used in the glyoxylic reaction.

19 Claims, No Drawings

REAGENT AND METHOD FOR DETERMINATION OF GLOBULIN

BACKGROUND OF THE INVENTION

This invention relates to a reagent and method for determining total globulin in biological fluids, and in particular to improvements in the glyoxylic reaction for determination of tryptophan or tryptophan-containing proteins.

Determining the total quantity of globulins in a biological fluid, such as serum or plasma, is important in the diagnosis of certain disease states. It is also important in the commercial production and purification of globulins.

The traditional clinical method of determining total globulin in a biological sample, such as serum, has been initial determination of total protein, for example by the biuret reaction, followed by delicate chemical fractionation to precipitate the globulin component, and followed determination of the remaining albumin. Globulin content is then calculated as the difference between these values. The difficulties of the traditional method may be overcome by determining globulin directly. Because the so-called glyoxylic (or Hopkins-Cole) reaction is specific for tryptophan and certain tryptophan derivatives, and because globulin is the only substantial source of tryptophan in serum and many other biological fluids, the glyoxylic reaction provides a convenient direct globulin determination which does not require pretreatment of the sample.

Hopkins and Cole, Proc. Roy. Soc., 68, 21 (1901) and J. Physiol. 27, 418 (1902) indicated that the purple color which was produced by the "Adamkiewicz protein reaction" using a reagent mixture consisting of sulfuric acid and acetic acid was due to the presence of tryptophan or tryptophan-containing protein, and that the essential component which initiated the "Adamkiewicz reaction" was the glyoxylic acid which originated as an impurity from the employed acetic acid. Based upon this observation, Hopkins and Cole renamed the "Adamkiewicz reaction" the "glyoxylic reaction".

Fearon, Biochem, J., 14, 548 (1920), further studied the glyoxylic reaction. He replaced sulfuric acid (which he found to be unsuitable) with acetic acid saturated with HCl gas; phosphoric acid was said to have been used in a few unspecified cases. His work utilized indole, scatole and carbazole in addition to tryptophan. He concluded that the overall glyoxylic reaction is the result of two distinct chemical reactions:

a. a condensation reaction between two molecules of tryptophan or 3-substituted tryptophan derivative and one molecule of glyoxylic acid to form a molecule of condensation product, designated as the leuco base, and a molecule of water, and b. an oxidation reaction in which the leuco base formed by the initial condensation reaction undergoes oxidation in the presence of air to form a molecule of colored product and another molecule of water in the reaction mixture. Fearon represented these two reactions as follows:

a. CONDENSATION REACTION

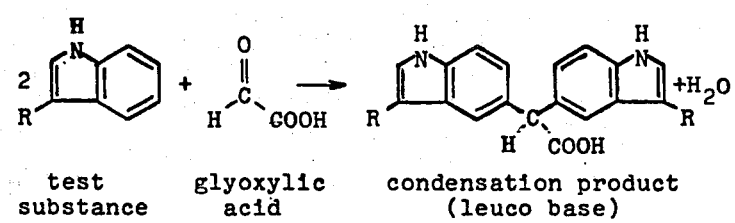

test substance     glyoxylic acid     condensation product (leuco base)

b. OXIDATION REACTION

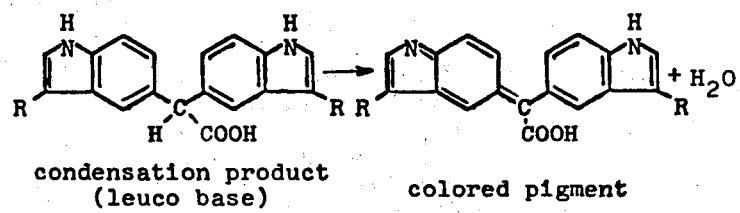

condensation product (leuco base)     colored pigment

It is evident from the above representation that the overall glyoxylic reaction requires two moles of test substance and one mole of glyoxylic acid to form one mole of colored derivative and two moles of water, and that the final color produced by the glyoxylic reaction is dependent upon the extent to which the condensation and oxidation reactions are favored in the reaction mixture.

In accordance with Fearon's formulation of the glyoxylic reaction, the function of sulfuric acid is to initiate the condensation reaction that results in the formation of leuco base. However, sulfuric acid also exerts a charring effect on the reactants and thus interferes with their ability to produce the leuco base. To minimize the charring action of sulfuric acid and to reduce the viscosity of the reaction mixture, glacial acetic acid is generally used as a diluent. This, however, impairs the condensing activity of sulfuric acid as well as decreasing the solubility of the test specimen (particularly protein) in the reaction mixture.

The reaction in which the leuco base undergoes oxidation by molecular oxygen of air in the presence of sulfuric acid (which also acts as an oxidizing agent in a variable manner) to form the purple color pigment, is rather sensitive, selective, and sluggish. For example, if the reaction mixture incorporates a strong oxidizing agent, the desired purple colored pigment undergoes further oxidation to form products of nonspecific colors. On the other hand, if the reaction mixture contains only weak oxidizing agents, the purple color formation is not stimulated. Moreover, water formed during the selective oxidation of leuco base also hydrolyzes the purple color generated by the reaction.

From the foregoing discussion, it seems that the final or net color produced in the glyoxylic reaction mixture depends upon the extent to which various desirable and undesirable reactions are favored by the employed reagents, their concentrations, and the reaction conditions.

Ever since the discovery of the glyoxylic reaction, various methods have been developed from time to time for the determination of free tryptophan or proteins containing tryptophan, such as globulins, in biological fluids. These methods employed sulfuric or perchloric acid (both may cause charring) as the condensing agent and glacial acetic acid as the diluent. They also generally add glyoxylic acid and a "sensitizing agent", which appears to facilitate the oxidation reaction. An amount of glyoxylic acid which provides a measurable reaction color proportional to globulin concentration has been termed a "colorimetric amount" of glyoxylic acid. Likewise, an amount of sensitizing agent which detectably enhances the reaction color without masking it has been termed a "sensitizing amount" of the sensitizing agent. Winkler, Z. Physiol. Chem., 288, 50 (1934) employed copper sulfate as a "sensitizing agent". Copper sulfate was subsequently also used by Goldenberg and Drewes, Clin. Chem., 17, 358 (1971), by Goldenberg, U.S. Pat. No. 3,607,081 (1971), and by Shaw and McFarlane, Can. J. Res., 16, 361 (1938). It has been reported that copper sulfate masks the glyoxylic reaction color and also tends to precipitate in the presence of concentrated sulfuric acid. Saifer and Gerstenfeld, Clin. Chem., 10, 970 (1964) replaced sulfuric acid and copper sulfate with perchloric acid and potassium persulfate but this initiated the formation of nonspecific color in the glyoxylic reaction mixture.

Opienska-Blauth et al, Anal. Biochem., 6, 69 (1963), considered added glyoxylic acid to be labile in contact with the sulfuric acid present in the reaction mixture. To avoid this problem, these investigators did not add glyoxylic acid to their reaction mixture. Instead, they employed separate acetic acid and sulfuric acid reagents and added a small amount of ferric chloride to the acetic acid to generate glyoxylic acid in situ, since trivalent iron is known to catalyze the oxidation of acetic acid to glyoxylic acid in the presence of sulfuric acid. These investigators added a substantial amount of water (about twenty percent) to their reaction mixture.

Although several methods have been described for the estimation of free tryptophan or tryptophan-containing proteins, these methods have failed to produce reproducible results and have lacked sensitivity. This could be due to the considerable variations in the reaction conditions, as well as in the composition and water content of the final assay systems that were used in these methods. Because of the instability of the reagent or reagents employed by these methods, and the dependence of the methods on the precise concentrations of the reactants, prior methods have generally required recalibration for each set of determinations made.

SUMMARY OF THE INVENTION

One of the objects of this invention is to provide an improved modification of the glyoxylic reaction which facilitates both the condensation and oxidation reactions by counteracting the various undesirable reactions that are initiated by the reagents generally used in the glyoxylic reaction.

Another object is to maximize the sensitivity, and hence the purple color formation, in the glyoxylic reaction resulting from the stimulated condensation and oxidation reactions.

Another object is to increase the reliability of the glyoxylic reaction as a quantitative test for tryptophan and trypotophan-containing compounds, and in particular as a simple, linear, accurate, and reproducible test for serum globulins.

Another object is to provide a stable, sensitive, one-piece reagent for use in the improved test.

Other objects will become apparent in light of the following description.

In accordance with this invention, generally stated, the sensitivity and reliability of the glyoxylic reaction, utilizing a one-piece reagent comprising sulfuric acid, acetic acid and glyoxylic acid, is greatly improved by the addition to the reagent of one or more of the following: ferric ion, phosphoric acid, and monomethyl ether of ethylene glycol. The effective ranges of concentrations of the added components are discussed hereinafter.

The approximate amounts of the various ingredients that compose the preferred embodiment of the new reagent are as follows: 60–70 volumes of glacial acetic acid; 10–20 volumes of monomethyl ether of ethylene glycol (Methyl Cellosolve); 5–15 volumes of phosphoric acid; 5–15 volumes of sulfuric acid; 0.2–1.2 volumes of 20% glyoxylic acid solution (aqueous); and 0.4–1.2 volumes of 10% $FeCl_3 \cdot 6H_2O$ solution (aqueous). The presently preferred reagent system has the following approximate composition: glacial acetic acid, 65.0 ml; Methyl Cellosolve, 15.0 ml; ortho phosphoric acid, 10.0 ml; concentrated sulfuric acid, 10.0 ml; water, 1.2 ml; 0.3 millimoles of $Fe^{+++}$ ion; and 0.9 millimoles glyoxylic acid, respectively, per 100 ml of the final reagent mixture.

The present reagent system readily dissolves mixtures of albumin and globulin, and selectively, reacts with the dissolved globulin to form an intense purple color with an absorption maximum at 560 m$\mu$. The purple color thus formed attains a maximum intensity upon heating the reaction mixture, preferably to a temperature between 90°–96° C for about 3–7 minutes. The measured intensity of the maximum color is found to be proportional to the globulin concentration in the reaction mixture, and it remains unaltered for hours on standing at room temperature.

To determine the globulin concentration in the assay sample, the purple color of the reaction mixture can be conveniently measured at 560 m$\mu$, for example spectrophotometrically using a narrow band spectrophotometer or photometrically using a filter type photometer that transmits light between 530–590 m$\mu$. The measured optical density (or percent transmittance) can then be compared with a calibration curve or with a globulin standard solution treated simultaneously with the assay sample.

It has been found that biological fluids such as serum, containing mixtures of albumin, globulins, and non-protein fractions are capable of mixing with the sensitive reagent mixture in any proportions. The reagent mixture selectively reacts with the dissolved globulin to form a purple color, the intensity of which is proportional to the amount of total globulin, and is not influenced by the amounts of albumin and non-protein materials that are present in the reaction mixture.

The purple colored reaction product derived from the glyoxylic reaction using the present reagent system is found to be remarkably resistant to hydrolysis. Thus, the system offers great flexibility in the assay of globulins in samples that are either too high or too low in globulin concentration. Up to about five percent added water, by volume of the ultimate reaction mixture, reduces color by a clinically insignificant amount. As a consequence, different samples containing the same amount of globulin but having volumes of from about 0.02 ml to about 0.25 ml yield substantially the same measured color intensities when the final volume of the reaction mixture is maintained at 5 ml.

Moreover, the system will tolerate 15% or more added water by volume of the ultimate reaction mixture, although at these higher dilutions globulin concentration must be determined by reference to a standard containing a similar amount of added water. By way of example, with a sample containing 0.03% globulin, 0.75 ml of the sample in 5.0 ml of reaction mixture would yield an optical density (19 mm. light path) of about 0.13. This is several times the optical density obtained with a similarly diluted prior art system.

The research leading to the present invention indicates that the extent to which the glyoxylic reaction is sensitized is dependent on four factors: (a) composition of the solvent mixture present in the reaction medium, (b) sensitizing power and concentration of the sensitizing agent present in the reaction mixture, (c) concentration of glyoxylic acid present in the reaction mixture, and (d) water content of the reaction mixture.

The condensing activity of sulfuric acid in the glyoxylic reaction mixture is superior to that of phosphoric acid. However, the overall condensing and the charring activity of the sulfuric acid in the glyoxylic reaction mixture is dependent on the nature and amount of diluent that is present in the reaction mixture. It has been found that the addition of phosphoric acid, in a ratio of phosphoric acid to sulfuric acid of about 1:1, greatly increases the sensitivity of the glyoxylic reaction, when the mixture is included in the reagent system in a ratio to acetic acid of from about 10:90 to about 30:70. The ratio of phosphoric acid to sulfuric acid in the mixture should preferably not be below about 1:3, in order to avoid reduction of color. When the ratio is above about 3:1, the color is also reduced.

It has also been found that the sensitivity of the reagent system containing phosphoric acid is substantially increased by replacing a substantial amount of the acetic acid in the solvent mixture with Methyl Cellosolve (mono methyl ether of ethylene glycol). Neither ethylene glycol nor other derivatives of ethylene glycol (such as the ethyl or butyl ethers) have been found to have this property. Methyl Cellosolve also reduces the viscosity of the reagent and makes it more suitable for quantitative tests.

The solvent mixture which permits the maximum sensitization of the glyoxylic reaction has the following approximate proportions: acetic acid 6.5, phosphoric acid 1.0, Methyl Cellosolve 1.5, sulfuric acid 1.0. In the presence of a sensitizing agent, a glyoxylic reaction mixture containing one volume of sulfuric acid to nine volumes of acetic acid/phosphoric acid/Methyl Cellosolve (6.5:1.0:1.5) produces a color which is about three times stronger than the color that is produced by a reaction mixture containing one volume of sulfuric acid to nine volumes of acetic acid under similar reaction conditions. This suggests that the acetic acid/phosphoric acid/Methyl Cellosolve mixture possesses the ability to stimulate the overall glyoxylic reaction by promoting both the condensation and oxidation reactions, as well as to minimize the charring activity, of the sulfuric acid present in the glyoxylic reaction mixture.

It has also been discovered that ferric chloride possesses the ability to sensitize the glyoxylic reaction under proper conditions. In fact, ferric ion in the present reagent system possesses a sensitizing power or activity which is substantially stronger than cupric ion under similar reaction conditions. Moreover, ferric ion in the glyoxylic reaction mixture does not mask the glyoxylic color. Also, the ferric ion in the reagent does not precipitate on storage. In the presence of excess water, ferric chloride has been found to desensitize the glyoxylic reaction. This suggests that in the absence of the water absorbing system discussed more fully hereinafter, and in the absence of phosphoric acid, ferric chloride acts as a strong oxidizing agent that further oxidizes the purple color derived from the glyoxylic reaction to a colorless one and thus decreases the sensitivity of the glyoxylic reaction.

The ability of phosphoric acid to form complexes is also believed to play a large part in the sensitizing power of sensitizing agents, such as ferric ion, in the present reagent system. The efficiency of a sensitizing agent seems to increase as its position in the electrochemical series becomes closer to oxygen. The difference in the standard reduction potential between $Fe^{+++}(H_3PO_4)$ and $O_2$ is minimum (0.438 − 0.401 = 0.037). The difference in the standard reduction potential between $Cu^{++}$ and $O_2$ is 0.061 (0.340 − 0.401). The difference in standard reduction potential between $Fe^{+++}$ (0.5f $H_2SO_4$) and $O_2$ is 0.278 (0.679 − 0.401).

The glyoxylic reaction mixture requires an excess concentration of glyoxylic acid for the maximum color formation. As a result, the sensitive reagent mixture has been formulated to contain an excess of glyoxylic acid. Moreover, the added $Fe^{+++}$ ion in the reagent mixture catalyzes the formation of glyoxylic acid in it, and thus maintains a steady supply of glyoxylic acid in the reagent during storage at room temperature. As a consequence, the sensitivity of the reagent remains substantially unaltered even after a prolonged storage period.

The sensitivity of the glyoxylic reaction to the presence of water in the reaction mixture is believed to be related to two factors: (1) the tendency of water to decrease the condensing activity of sulfuric acid, and (2) hydrolysis of the colored pigment produced by the oxidation of the leuco base. The reagent mixture of the present invention is formulated with minimal added water, about 1.5 ml per 100 ml of the reagent system, not including the bound water in the phosphoric acid component. More importantly, the strong water-absorbing properties of the phosphoric acid and Methyl Cellosolve preclude the presence of substantial amounts of free water in the reaction mixture even when the reaction mixture contains up to fifteen percent added water. Their water-absorbing properties are thus believed to be responsible for the extraordinary tolerance of the reagent to variations in the amount of water in the reaction mixture, as previously described. This analysis is perhaps confirmed by the observation that over a long period of storage and use, the resistance of the reagent system to water may decrease somewhat, probably because of absorption of water from the atmosphere.

DESCRIPTION OF THE PREFERRED EMBODIMENT

The following examples are illustrative of the preferred reagent composition of this invention and of the improved globulin determination using it.

In the Examples, the following reagents, materials and instrument were used except as otherwise identified:

a. Concentrated Sulfuric Acid: 96.5%, Sp. Gr. 1.84;
b. Ortho Phosphoric Acid: 85.0%, Sp. Gr. 1.7;
c. Glacial Acetic Acid: 99.7%;
d. 20% Glyoxylic Acid Solution (aq.): 2.2 millimoles/ml;
e. 10% Ferric Chloride Solution (aq.): 0.37 millimoles $Fe^{+++}$/ml;
f. 9.2% Copper Sulfate Solution (aq.): 0.37 millimoles $Cu^{++}$/ml;
f¹. 12.5% Copper Sulfate Solution (aq.): 0.50 millimoles $Cu^{++}$/ml;
g. Total Protein Standard Solution: 8.0 gm. total protein/100 ml (3.0 gm. human serum globulin ($\gamma$) and 5.0 gm. human serum albumin/100 ml);
h. Human serum samples derived from a local hospital.
i. Instrument: Coleman Jr. II and 19 mm matched cuvets.

In order to determine the conditions that influence the maximum color formation by the glyoxylic reaction, and to illustrate the usable compositions of a suitable one-piece reagent system in accordance with the present invention, different reagent mixtures of known compositions were prepared as described in Examples 1–6. For the determination of the glyoxylic reaction activities of these reagent mixtures, the following standard procedure was adopted: 5.0 ml of the specific reagent mixture was mixed with 0.03 ml of the Total Protein Standard Solution (0.9 mg. human $\gamma$-globulin). The mixture was then heated for 5.0 mins. in a water bath maintained at 90°–96° C to complete the glyoxylic reaction. After the reaction mixture was cooled, its color intensity was measured at 560 m$\mu$ using the same specific reagent mixture for the blank. The measured $OD_{560}$ of the reaction mixture was then taken as the glyoxylic reaction activity of the specific reagent mixture. Certain reagent mixtures were found to be incapable of dissolving the test material completely. As a result, the corresponding reaction mixture showed turbidity. To measure the color intensities of turbid reaction mixtures, corresponding turbid unheated reaction mixtures were used as blanks since these turbid unheated reaction mixtures were found to produce negligible glyoxylic color during the experimental period.

EXAMPLE 1

In order to determine the effect of sulfuric acid concentration on the glyoxylic reaction, and to compare simultaneously the sensitizing or oxidizing activities of ferric and cupric ion under the employed reaction conditions, three sets of reagent mixtures were prepared. Each set contained 100 milliliters of a mixture of Concentrated Sulfuric Acid and Glacial Acetic Acid, in the proportions shown in Table 1. Each set also contained 0.8 milliliters of 20% Glyoxylic Acid Solution (1.74 millimoles glyoxylic acid). To compare the sensitizing or oxidizing activities of ferric and cupric ions, Set A of reagent mixtures contained 0.4 milliliters of 10% Ferric Chloride Solution (0.148 millimoles ferric ion); Set B contained 0.4 milliliters of 9.2% cupric sulfate solution (0.148 millimoles cupric ion); Set C contained 0.4 milliliters of water. Table 1 sets out the activity ($OD_{560}$) recorded when each reagent mixture was utilized to carry out the glyoxylic reaction on the total protein standard solution in accordance with the standard procedure:

Table I

| Parts by Volume Sulfuric Acid to Acetic Acid | Set A ($Fe^{+++}$) | Set B ($Cu^{++}$) | Set C (No Sensitizing Agent) | Remarks |
|---|---|---|---|---|
| 00:100 | — | — | — | Turbid |
| 10:90 | .24 | .16 | .10 | Turbid |
| 20:80 | .37 | .22 | .13 | Clear |
| 30:70 | .30 | .19 | .14 | Clear |
| 50:50 | .14 | .10 | .07 | Clear |

Table I shows that a low concentration of sulfuric acid is not favorable for the glyoxylic reaction, as the added test substance in the reaction mixture remains insoluble and causes turbidity in it. On the other hand, a high concentration of sulfuric acid reduces the color formation in the reaction mixture, perhaps because of its increased charring effect on the test substance and glyoxylic acid. It appears from Table I that the approximate ratio of sulfuric acid to acetic acid which is favorable for maximum color formation and solubility of serum proteins under the employed conditions is 2:8.

Table I also shows that either ferric or cupric ion is capable of sensitizing the glyoxylic reaction and that under the reaction conditions of this Example the sensitizing power of the ferric ion is considerably greater than that of the cupric ion. It is also evident from Table I that reaction mixtures not containing cupric ion or ferric ion are capable of producing partial color.

EXAMPLE 2

A series of determinations was made to ascertain the effect of substituting phosphoric acid for the sulfuric acid used in Example 1. Three sets of reagent mixtures, labeled D, E, and F, were prepared which differed from the respective sets A, B, and C of Example 1 only in the substitution of phosphoric acid for sulfuric acid. In addition, each set included a reagent mixture in which all of the acetic acid was replaced with phosphoric acid. Table II sets out the activity recorded when each reagent mixture was utilized to carry out the glyoxylic reaction on the total protein standard solution in accordance with the standard procedure:

Table II

| Parts by Volume Phosphoric Acid to Acetic Acid | Set D ($Fe^{+++}$) | Set E ($Cu^{++}$) | Set F (No Sensitizing Agent) | Remarks |
|---|---|---|---|---|
| 00:100 | — | — | — | Turbid |
| 10:90 | .04 | .04 | .02 | Turbid |
| 20:80 | .06 | .05 | .02 | Clear |
| 30:70 | .07 | .08 | .03 | Clear |
| 50:50 | .18 | .12 | .04 | Clear |

Table II-continued

| Parts by Volume Phosphoric Acid to Acetic Acid | Set D ($Fe^{+++}$) | Set E ($Cu^{++}$) | Set F (No Sensitizing Agent) | Remarks |
| --- | --- | --- | --- | --- |
| 100:00 | .20 | .16 | .09 | Clear |

It will be seen that in the presence of a sensitizing agent the glyoxylic reaction occurs even when phosphoric acid is substituted for sulfuric acid, and that the activity shown by the reagent mixture increases as the phosphoric acid concentration increases. However, even at the highest phosphoric acid concentration, the overall activity of these mixtures is less than the corresponding mixtures utilizing twenty percent sulfuric acid. The sensitizing effect of ferric ion is somewhat greater than that of cupric ion. Without a sensitizing agent, the activity of the reagent is negligible.

EXAMPLE 3

Equal volumes of sulfuric acid and phosphoric acid were mixed. Three sets of reagent mixtures, labeled G, H, and I, were prepared. These sets differed from the respective sets D, E, and F of Example 2 only in the substitution of the 1:1 mixture of sulfuric acid and phosphoric acid for the phosphoric acid of Example 2. Table III sets out the activity recorded when each reagent mixture was utilized to carry out the glyoxylic reaction on the total protein standard solution in accordance with the standard procedure:

Table III

| Parts by Volume Sulfuric Acid/Phosphoric Acid Mixture to Acetic Acid | Set G ($Fe^{+++}$) | Set H ($Cu^{++}$) | Set I (No Sensitizing Agent) | Remarks |
| --- | --- | --- | --- | --- |
| 00:100 | — | — | — | Turbid |
| 10:90 | .51 | .32 | .05 | Turbid |
| 20:80 | .57 | .33 | .13 | Clear |
| 30:70 | .48 | .26 | .15 | Clear |
| 50:50 | .32 | .21 | .13 | Clear |
| 100:00 | .27 | .20 | .14 | Clear |

Table III shows that under the employed reaction conditions, in the presence of a sensitizing agent, a concentration of from 10% to 30% of the sulfuric acid/phosphoric acid mixture produces a color which is considerably stronger than the color produced by either sulfuric acid or phosphoric acid alone. The reagent mixture containing 20 parts of the sulfuric acid/phosphoric acid mixture produces a non-turbid reaction mixture and also produces the most intense color. The sensitizing effect of ferric ion is, as in Example 1, considerably greater than that of cupric ion.

EXAMPLE 4

The effect of substituting the mono methyl ether of ethyleneglycol (Methyl Cellosolve) for some or all of the acetic acid used as diluent in the previous Example was determined by preparing three sets of reagent mixtures, labeled J, K, and L, which were similar to the corresponding reagents G, H, and I of Example 3. Each of the sets J, K, and L, however, contained 20 parts of the 1:1 mixture of sulfuric acid and phosphoric acid to 80 parts diluent. The ratio of Methyl Cellosolve to acetic acid in the diluent was varied in each set of reagent mixture as set out in Table IV, which shows the activity recorded when each reagent mixture was utilized to carry out the glyoxylic reaction as in the preceding Examples.

Table IV

| Parts by Volume Methyl Cellosolve to Acetic Acid | Set J ($Fe^{+++}$) | Set K ($Cu^{++}$) | Set L (No Sensitizing Agent) | Remarks |
| --- | --- | --- | --- | --- |
| 00:80 | .61 | .32 | .14 | Clear |
| 5:75 | .65 | .38 | .16 | Clear |
| 15:65 | .73 | .42 | .15 | Clear |
| 40:40 | .48 | .22 | .14 | Clear |
| 50:30 | .18 | .05 | .05 | Turbid |
| 70:10 | .03 | .02 | — | Turbid |
| 80:00 | — | — | — | Turbid |

Table IV shows that the replacement of a minor part of the acetic acid with Methyl Cellosolve increases the color intensity as compared with the preceding Example, but only in the presence of a sensitizing agent. When half or more of the acetic acid is replaced with Methyl Cellosolve, the color intensity is reduced and the reaction mixture loses its clarity.

The foregoing Examples 1–4 indicate that a highly suitable solvent mixture for the glyoxylic reaction contains sulfuric acid, phosphoric acid, acetic acid, and Methyl Cellosolve in the approximate volumetric ratio of 10:10:65:15.

EXAMPLE 5

A series of experiments was made to determine the optimum amount of added glyoxylic acid in the preferred reagent mixture containing cupric ion or ferric ion and a solvent mixture consisting of sulfuric acid, phosphoric acid, acetic acid, and Methyl Cellosolve in the volumetric ratio of 10:10:65:15. Because the acetic acid reagent is contaminated with a variable quantity of glyoxylic acid, the results of this series of experiments can be regarded as only a general indication of the effect of glyoxylic acid concentration. Two sets of reagent mixtures were prepared, each containing the preferred solvent mixture. Set M contained 0.148 millimoles of ferric ion, and Set N contained 0.148 millimoles of cupric ion. The quantity of added glyoxylic acid (expressed as millimoles per 100 ml of reagent mixture) was varied as set out in Table V, which shows the activity recorded when each reagent mixture was utilized to carry out the glyoxylic reaction as in the preceding Examples.

Table V

| Glyoxylic Acid (millimoles added/100 ml.) | Set M ($Fe^{+++}$) | Set N ($Cu^{++}$) | Remarks |
| --- | --- | --- | --- |
| 0.00 | .55 | .45 | Clear |
| 0.43 | .73 | .50 | Clear |
| 0.87 | .72 | .46 | Clear |
| 1.30 | .70 | .43 | Clear |
| 1.74 | .70 | .42 | Clear |

Table V shows that considerable glyoxylic acid was present in the acetic acid employed, and that approximately 0.43 milliliters of added glyoxylic acid per 100 milliliters of reagent mixture produced maximum color using this reagent. It was concluded that 0.87 millimoles of glyoxylic acid per 100 milliliters of reagent mixture (0.4 ml of reagent d) is a more suitable concentration than that used previously. Therefore, this concentration was used in the following Examples.

EXAMPLE 6

Two sets of reagent mixtures labeled Set O and Set P, were prepared using the preferred solvent mixture and 0.4 milliliters of glyoxylic acid reagent (0.87 millimoles glyoxylic acid) per 100 ml. of solvent. Each reagent mixture also contained 0.8 ml of either a ferric chloride solution (Set O) or a copper sulfate solution (Set P) per 100 ml of reagent mixture. The millimoles of ferric ion or cupric ion added to each reagent mixture are shown in the following Table VI, which shows the activity recorded when each reagent mixture was utilized to carry out the glyoxylic reaction as in the previous Examples:

Table VI

| Sensitizing Agent (millimoles/100 ml.) | Set O ($Fe^{+++}$) | Set P ($Cu^{++}$) |
|---|---|---|
| 0.000 | 0.15 | 0.15 |
| 0.037 | 0.57 | 0.37 |
| 0.074 | 0.67 | 0.42 |
| 0.148 | 0.73 | 0.50 |
| 0.222 | 0.76 | 0.52 |
| 0.296 | 0.74 | 0.53 |
| 0.400 | — | 0.52 |

It will be seen that a concentration of from about 0.15 to 0.30 millimoles per 100 ml of reagent mixture is desirable for both ferric ion and cupric ion. The ferric ion produces a substantially higher maximum activity than the cupric ion, and also produces maximum glyoxylic reaction activity at a somewhat lower molar concentration than does the cupric ion.

EXAMPLE 7

In this and the following Examples, preferred reagent mixtures for the glyoxylic reaction were used which had the following composition: (a) glacial Acetic Acid, 65.0 ml; (b) Methyl Cellosolve, 15.0 ml; (c) Ortho Phosphoric Acid (85%), 10.0 ml; (d) Concentrated Sulfuric Acid (96%), 10.0 ml; (e) Aqueous Glyoxylic Acid Solution (20%), 0.4 ml (.9 millimoles); (f) Aqueous Ferric Chloride ($FeCl_3.6H_2O$) Solution (10%), 0.8 ml (.3 millimoles), or Aqueous Copper Sulfate ($CuSO_4.5H_2O$) Solution (9.2%), 0.8; ml (.3 millimoles). For convenience, the preferred reagent mixture containing ferric ion will be designated as Reagent Q hereinafter, while the reagent mixture containing cupric ion will be designated as Reagent R.

It is found that both Reagents Q and R are equally capable of dissolving protein and non-protein material present in bioligical fluid, particularly in serum. The dissolved tryptophan-containing protein, especially the globulin fraction of serum, selectively reacts with the reagent to form an intense purple color with an absorption maximum at 560 m$\mu$. The purple color thus formed attains a maximum intensity upon heating the reaction mixture.

Reagents Q and R were utilized to carry out the glyoxylic reaction according to the method of Examples 1–6, except that the heating time at 90°–96° C was varied as shown in Table VII:

Table VII

| Heating Time (Mins.) | Reagent Q | Reagent R |
|---|---|---|
| 1.0 | .59 | .19 |
| 3.0 | .75 | .48 |
| 5.0 | .76 | .52 |
| 7.0 | .70 | .54 |
| 9.0 | .71 | .54 |

It will be seen from Table VII that an extended heating period does not significantly influence the maximum color produced in the reaction mixture containing either Reagent Q or Reagent R, and that the measured color intensities of reaction mixtures containing Reagent Q are considerably higher than the reaction mixtures containing Reagent R. It is also found that maximum color formed in the reaction mixture, whether containing Reagent Q or Reagent R, is proportional to globulin concentration, and it remains stable for hours on standing at room temperature. In the following Examples, a heating time of five minutes was retained.

EXAMPLE 8

The effect of added water on Reagent Q and Reagent R was investigated, as shown in Table VIII. Each reagent mixture contained 0.02 ml of the globulin standard (0.6 mg of globulin), a variable amount of added water as shown, and sufficient of the reagent mixture to make 5.0 milliliters of reaction mixture. The activities recorded are set out in Table VIII.

Table VIII

| Added Water | Reagent Q | Reagent R | % Color Loss Reagent Q | % Color Loss Reagent R |
|---|---|---|---|---|
| 0% | 0.49 | 0.40 | 0 | 0 |
| 5% | 0.48 | 0.39 | 2 | 2.5 |
| 10% | 0.46 | 0.32 | 6 | 21.0 |
| 15% | 0.34 | 0.19 | 31 | 53.0 |
| 20% | 0.23 | 0.08 | 49 | 86.0 |
| 25% | 0.13 | 0.03 | 74 | 93.0 |

It will be seen from Table VIII that the preferred reagent mixture containing ferric ion lost less than 10% of its sensitivity when the reaction mixture contained 10% added water and lost only about one-third of its sensitivity when the reaction mixture contained 15% water. Expressed differently, if 0.75 ml of a bioloical fluid containing globulin is added to 4.25 ml of the preferred reagent, the resulting color is about twenty-five times as intense as if 0.02 ml of sample were added to 5.0 ml of the reagent mixture. A sample containing as little as 0.03% globulin, diluted in this way, will, therfore, produce an optical density at 560 m$\mu$ of approximately 0.13 (19 mm cuvet).

It will also be seen that the sensitivity of the reagent mixture of the present invention containing cupric ion, although more affected by dilution than the preferred reagent mixture containing ferric ion, nonetheless showed substantial sensitivity when diluted up to 15%.

EXAMPLE 9

Calibration curves were prepared for Reagents Q and R using the specified instrument with 19 mm cuvets and plotting absorbence at 560 m$\mu$ against globulin concentrations of 1, 2, 3, 4, and 5 grams of globulin per 100 ml of the test solution. Both reagents gave linear relations between absorbence and concentration, but the slope of the Reagent Q (ferric ion) curve was about 0.16 and the slope of the Reagent R (cupric ion) curve was about 0.12; i.e., the sensitivity of the Reagent Q is about 1.3 times that of the Reagent R.

EXAMPLE 10

The stability of the preferred Reagent Q of this invention (containing ferric ions) was studied over an extended period. Both before and after prolonged room temperature storage of two separate lots of the preferred Reagent Q, the activities of the two lots were substantially the same (slope of calibration curve equal to $0.160 \pm 0.005$ using the specified instrument with 19 mm cuvets). It thus appears that the reagent of this invention possesses an almost unlimited shelf life at room temperature. However, if a calibration curve is utilized to determine globulin concentrations, it should be checked regularly and should be redrawn for every new batch of the reagent mixture, in accordance with accepted laboratory procedure.

Based upon the foregoing studies, a sensitive method, using the preferred reagent mixture containing ferric ions (i.e., Reagent Q), has been developed for the direct estimation of total globulin in biological fluids, particularly in serum, without involving an initial fractionation procedure. The following Examples 11, 12 and 13 illustrate the use of the sensitive reagent for the estimation of total globulin in biological fluids containing a high or low concentration of the same.

EXAMPLE 11

Procedure for the Estimation of Total Globulin in Biological Fluids (Concentration Range 1.0–6.0 gm%)

Take three test tubes marked SAMPLE, STANDARD, and BLANK. To each tube add 5.0 ml of globulin reagent. Then add 0.02 ml of assay sample to the tube marked SAMPLE, 0.02 ml of total protein standard solution containing 3.0 and 5.0 gm% human $\gamma$-globulin and human albumin, respectively, to the tube marked STANDARD and 0.02 ml of 0.9% saline to the tube marked BLANK. Mix the contents of each tube well. Then heat the tubes in a water bath set at 90°–96° C for 5.0 minutes. At the end of heating period, cool the test tubes for two to three minutes in a cold water bath. Then measure the intensity of the color produced by the SAMPLE and the STANDARD at 560 m$\mu$, using the BLANK as the reference in any instrument that emits light at the indicated wavelength. The product of the measured ratio of $OD_{560}$ of SAMPLE to $OD_{560}$ of STANDARD, and the globulin concentration in the STANDARD determines the globulin concentration in the SAMPLE in gm%.

EXAMPLE 12

Procedure for the Estimation of Total Globulin in Biological Fluids (Concentration range 0.1–0.6 mg%)

Mark three test tubes SAMPLE, STANDARD, and BLANK. Add 5.0 ml globulin reagent to each tube. To the SAMPLE tube add 0.2 ml of assay sample. To the STANDARD and BLANK tubes, add 0.2 ml of tenfold diluted total protein standard solution and 0.2 ml of 0.9% saline, respectively. Follow the rest of the procedure in the manner described before.

Total Globulin (gm%) = $OD_{560}$ SAMPLE/$OD_{560}$ STANDARD × (concentration of Standard) × 1/10

EXAMPLE 13

Procedure for the Estimation of Total Globulin in Biological Fluids (Concentration range 0.05–0.3 gm%)

Use 0.4 ml of the assay sample and 0.4 ml of 20-fold diluted total protein standard solution for the color reactions as described before, and then calculate the Total Globulin concentration in the sample from the following equation:

Total Globulin (gm%) = $OD_{560}$ SAMPLE/$OD_{560}$ STANDARD × (concentration of Standard) × 1/20

EXAMPLE 14

The reproducibility of the sensitive method of this invention (as described in Example 11), utilizing the preferred reagent mixture, was tested on replicate samples of human serum. Serum pools with total globulin concentrations of 1.25, 1.83, 3.66 gm/100 ml were analyzed on thirty separate occasions. The corresponding standard deviations and coefficients of variation were calculated to be 0.062, 0.089, 0.124 gm/100 ml and 4.9, 4.8, 3.4%, respectively. Analysis of fifteen serum samples using the present method and the classical salt fractionation method gave a correlation coefficient of 0.988. Comparison of results obtained on twenty-two samples by the present method and a differential method based on direct determinations of total protein and of albumin in serum yielded a correlation coeffiecint of 0.993.

EXAMPLE 16

Recovery studies using the method of Example 11 were made. Total globulin concentrations of three different serum pools were increased from 2.11, 1.42, 3.49 gm/100 ml to 3.61, 2.92, 4.99 gm/100 ml, respectively. Recoveries ranged from 98% to 109%.

In light of the foregoing description, numerous variations in the reagent and method of the present invention, within the scope of the following claims, will occur to those skilled in the art.

I claim:

1. In a method of determining a tryptophan-containing protein by a modified glyoxylic reaction comprising mixing a minor amount of a biological fluid with a reagent composition comprising sulfuric acid, a diluent, a colorimetric amount of glyoxylic acid, and a sensitizing amount of a sensitizing agent, thereafter heating the mixture to develop a purple color, and thereafter measuring the depth of color formed, hence the amount of said tryptophan-containing protein present, the improvement wherein said reagent composition further comprises ortho-phosphoric acid in a ratio of ortho-phosphoric acid to sulfuric acid of about 3:1 to about 1:3, said sulfuric acid and ortho-phosphoric acid together comprising from about 10 to about 50 parts per 100 parts by volume of said reagent composition.

2. In a method of determining a tryptophan-containing protein by a modified glyoxylic reaction comprising mixing a minor amount of a biological fluid with a reagent composition comprising sulfuric acid, a diluent, a colorimetric amount of glyoxylic acid, and a sensitizing amount of a sensitizing agent, thereafter heating the mixture to develop a purple color, and thereafter measuring the depth of color formed, hence the amount of said tryptophan-containing protein present, the improvement wherein said reagent composition further comprises (a) ortho-phosphoric acid in a ratio of ortho-phosphoric acid to sulfuric acid of about 3:1 to about 1:3, said sulfuric acid and ortho-phosphoric acid together comprising from about 10 to about 50 parts per 100 parts by volume of said reagent composition, and (b) from 5 to 40 parts of monomethyl ether of ethylene glycol per 100 parts by volume of said reagent composition.

3. The improvement of claim 2 wherein said sensitizing agent comprises ferric ion.

4. The improvement of claim 2 wherein said sensitizing agent comprises cupric ion.

5. The improvement of claim 1 including the further improvement that said sensitizing agent comprises not less than 0.03 millimoles of ferric ion per 100 milliliters of said reagent composition.

6. The improvement of claim 1 wherein said sensitizing agent comprises not less than 0.03 millimoles of cupric ion per 100 milliliters of said reagent composition.

7. The improvement of claim 1 wherein the tryptophan-containing protein is globulin.

8. A reagent useful for the determination of globulin in biological fluids, comprising per 100 ml of said reagent:
 a. 50–90 ml acetic acid
 b. 5–25 ml sulfuric acid
 c. 5–25 ml ortho-phosphoric acid
 d. a colorimetric amount of glyoxylic acid
 e. a sensitizing amount of a sensitizing agent.

9. The reagent of claim 8 wherein said reagent comprises, per 100 ml of said reagent, about 10–30 milliliters of an approximately 1:1 mixture of sulfuric acid and phosphoric acid.

10. The reagent of claim 8 wherein said sensitizing agent has a standard reduction potential of from about 0.3 to about 0.5.

11. The reagent of claim 10 wherein the sensitizing agent comprises about 0.1 to about 0.7 millimoles of ferric ion.

12. A reagent useful for the determination of globulin in biological fluids, comprising per 100 ml of said reagent:
 a. 40–75 ml acetic acid
 b. 5–40 ml monomethyl ether of ethylene glycol
 c. 5–25 ml sulfuric acid
 d. 5–25 ml phosphoric acid
 e. a colorimetric amount of glyoxylic acid
 f. a sensitizing amount of a sensitizing agent.

13. The reagent of claim 12 wherein the sensitizing agent comprises about 0.1 to about 0.7 millimoles of ferric ion.

14. The reagent of claim 12 wherein said reagent comprises, per 100 ml of said reagent, about 10–30 combined milliliters of sulfuric acid and phosphoric acid, said sulfuric acid and phosphoric acid being present in a ratio of about 3:1 to about 1:3.

15. The improvement of claim 1 wherein said diluent comprises a short-chain fatty acid.

16. The improvement of claim 15 wherein said diluent is acetic acid.

17. The improvement of claim 2 wherein said diluent comprises a short-chain fatty acid.

18. The improvement of claim 17 wherein said diluent is acetic acid.

19. The improvement of claim 2 wherein the tryptophan-containing protein is globulin.

* * * * *